(12) United States Patent
Hvidkjær et al.

(10) Patent No.: US 12,150,628 B2
(45) Date of Patent: Nov. 26, 2024

(54) BIOPSY DEVICE (71) Applicant: TeesuVac ApS, Hørsholm (DK)

(72) Inventors: John Hvidkjær, Hørsholm (DK); Rasmus Kirkegaard, Hørsholm (DK); Jonas Hjerl Hansen, Hørsholm (DK)

(73) Assignee: TeesuVac ApS, Hørsholm (DK)

( * ) Notice: Subject to any disclaimer, the term of this patent is extended or adjusted under 35 U.S.C. 154(b) by 694 days.

(21) Appl. No.: 17/416,158

(22) PCT Filed: Dec. 19, 2019

(86) PCT No.: PCT/EP2019/086314
§ 371 (c)(1),
(2) Date: Jun. 18, 2021

(87) PCT Pub. No.: WO2020/127737
PCT Pub. Date: Jun. 25, 2020

(65) Prior Publication Data
US 2022/0071607 A1 Mar. 10, 2022

(30) Foreign Application Priority Data
Dec. 20, 2018 (EP) ..................................... 18214519

(51) Int. Cl.
A61B 10/02 (2006.01)
(52) U.S. Cl.
CPC ................................ *A61B 10/0275* (2013.01)
(58) Field of Classification Search
CPC .......... A61B 10/02; A61B 2017/00353; A61B 2017/00982; A61B 2017/320064;
(Continued)

(56) References Cited

U.S. PATENT DOCUMENTS 5,653,694 A * 8/1997 Powles .............. A61B 10/0283
604/411
6,506,165 B1 * 1/2003 Sweeney .......... A61B 5/150221
600/562
(Continued)

FOREIGN PATENT DOCUMENTS

CN 102217954 A 10/2011
CN 104188692 A 12/2014
(Continued)

OTHER PUBLICATIONS

International Search Report and Written Opinion of International Searching Authority for Application No. PCT/EP2019/086314, mailed Mar. 20, 2020 (10 pages).
(Continued)

*Primary Examiner* — Eric F Winakur
*Assistant Examiner* — Abel Seifu Abegaz
(74) *Attorney, Agent, or Firm* — Nixon Peabody LLP (57) ABSTRACT

A biopsy device having a biopsy needle including an outer cutting needle and an inner sample needle with a tissue compartment. The device can, during each sampling operation, displace the outer cutting needle and the inner sample needle between open and closed positions of the tissue compartment. The biopsy device includes a vacuum source and a valve system to provide a pressure decrease in the tissue compartment at each sampling operation. The vacuum source has the form of at least one initially pre-evacuated vacuum container, and the biopsy device, by means of the initial vacuum of the at least one initially pre-evacuated vacuum container, provides a pressure decrease in the tissue compartment of the inner sample needle at each one of a limited number of consecutive sampling operations.

12 Claims, 4 Drawing Sheets

(58) Field of Classification Search
CPC .... A61B 2010/0208; A61B 2010/0225; A61B 10/0233; A61B 10/0283
See application file for complete search history.

(56) References Cited

U.S. PATENT DOCUMENTS

2006/0173377 A1    8/2006  McCullough et al.
2011/0184312 A1    7/2011  Moran, Jr.
2020/0397990 A1* 12/2020  Cho .................. A61B 10/0283

FOREIGN PATENT DOCUMENTS

| | | |
|---|---|---|
| EP | 0966920 A2 | 12/1999 |
| EP | 1843705 B1 | 12/2011 |
| EP | 2775929 A1 | 9/2014 |
| GB | 2223409 A * | 4/1990 ......... A61B 10/0283 |
| WO | WO 96/032147 A1 | 10/1996 |
| WO | WO 99/048425 A1 | 9/1999 |
| WO | WO 2013/068017 A1 | 5/2013 |

OTHER PUBLICATIONS

Chinese Patent Office; Examination Report in related Chinese Patent Application No. 201980084848.8, dated Dec. 27, 2023 (6 pages).

* cited by examiner

BIOPSY DEVICE

CROSS-REFERENCE TO RELATED APPLICATIONS

This application is a U.S. National Stage of International Application No. PCT/EP2019/086314, filed Dec. 19, 2019, which claims the benefit of European Patent Application No. 18214519.3, filed Dec. 20, 2018, both of which are incorporated herein by reference in their entireties.

The present invention relates to a biopsy device including a housing and a biopsy needle extending from the housing, the biopsy needle including an outer cutting needle and an inner sample needle with a tissue compartment for receiving a tissue sample, the outer cutting needle surrounding the inner sample needle, the outer cutting needle and the inner sample needle being arranged slidingly in relation to each other along their longitudinal direction, the outer cutting needle having a cutting end distant from the housing, the biopsy device being adapted to, during each sampling operation whereby a tissue sample is collected in the tissue compartment of the inner sample needle, displace the outer cutting needle and the inner sample needle at least between an open position of the tissue compartment in which the tissue compartment extends beyond the cutting end of the outer cutting needle and a closed position of the tissue compartment in which the outer cutting needle covers the tissue compartment, the biopsy device including a vacuum source for providing a pressure decrease in the tissue compartment of the inner sample needle via a vacuum channel arranged longitudinally in the biopsy needle, and the biopsy device including a valve system adapted to provide a pressure decrease in the tissue compartment at each sampling operation.

WO 99/48425 discloses a fine needle sample collection device for acquiring body samples by aspiration into an evacuated container. The device comprises a front hollow needle portion to be inserted into the body from which a sample is to be taken; a rear hollow needle portion for communicating with the evacuated container; a conduit connecting the front needle portion to the rear needle portion; and a valve mechanism to open and close the conduit. The valve mechanism is manually operable by one hand and controls the application of negative pressure in the front needle portion. The conduit may comprise a flexible tube and the valve mechanism may comprise releasable means to pinch the flexible tube in a pressure-tight manner. In use, the valve mechanism is actuated for sufficient time, and repeatedly if desired, to apply negative pressure in the front needle portion so as to draw a sample through the front needle portion through the conduit to the rear needle portion and into the pre-evacuated container.

WO 96/32147 discloses an aspiration fine needle apparatus for collecting cell samples from tissue, comprising a vacuum container having an enclosed evacuated space evacuated to a sub-ambient pressure and sealed by a penetrable diaphragm. An adapter is provided having a recess which is adapted to receive the vacuum container. A needle assembly is carried by the adapter and has a distal extremity serving as an aspiration needle to collect the cell sample. The proximal extremity of the needle assembly is disposed in said recess and is capable of penetrating the diaphragm of the vacuum container to couple the evacuated space to the flow passage of the needle assembly to supply a sub-ambient pressure to the distal extremity of the needle assembly. An on/off mechanism is carried by the adapter and includes a member engaged by the vacuum container and mounted in the recess for axial movement in the recess.

EP 2 775 929 A1 (TeesuVac ApS) discloses a handheld device for extracting tissue samples including a core needle arrangement and control arrangement. The needle arrangement has a cutting needle, a sample extraction needle, and a first end for inserting into tissue. The cutting needle has a cutting edge for cutting the tissue sample. The sample extraction needle has a side opening for receiving the tissue. The control arrangement has a vacuum generation chamber in fluid communication with the sample extraction needle in order to facilitate suction of tissue in the vicinity of the side opening of the sample extraction needle into the tissue sample chamber. Thereby, the handheld device and the tissue are ready for the cutting needle to cut the tissue sample from the tissue, which may be performed by said cutting needle moving back over said side opening. The vacuum generation chamber has a first member and a second member that move relative to each other. The first member is mechanically connected to the cutting needle. The handheld device is configured so that movement between the first and second members to increase volume of the vacuum chamber thereby reduces pressure in the sample extraction needle, induces movement between the cutting needle and the sample extraction needle to expose the side opening. The device may be driven by an electric motor, preferably connected to a battery. However, the movable members of the vacuum generation chamber may result in a relatively complicated construction. In particular in the case of a single-use device, there may be a need for a simpler construction in order to reduce production costs.

EP 1 843 705 B1 discloses a core needle biopsy device for taking tissue samples, including a housing containing an electric power source and a tension slide connected to the power source, the tension slide being brought into a cocked position against the action of a spring by the power source. A biopsy cannula unit is arranged on the tension slide, the biopsy cannula unit including a hollow biopsy cannula with a sample removal chamber and a cutting sheath. The biopsy device includes a vacuum pressure generating device, a valve, a first connection element connecting the biopsy cannula unit and the valve, and a second connection element connecting the valve and the vacuum pressure generating device. The cannula may be inserted into a body of tissue within a patient to extract a sample of the tissue of interest. Once the sample tissue is pulled within the tissue chamber in the cannula through suction, the chamber is closed, severing the sample tissue from the patient's body. The cannula may then be removed from the patient's body.

The object of the present invention is to provide a biopsy device for performing core needle biopsy being of simpler construction.

In view of this object, the vacuum source has the form of at least one initially pre-evacuated vacuum container, and the biopsy device is adapted to, by means of the initial vacuum of the at least one initially pre-evacuated vacuum container, provide a pressure decrease in the tissue compartment of the inner sample needle at each one of a limited number of consecutive sampling operations.

In this way, by providing the pressure decrease in the tissue compartment by means of the at least one initially pre-evacuated vacuum container, the number of moving parts may be reduced substantially compared to prior art vacuum assisted core needle biopsy devices. In particular, the need for an electric motor for driving a vacuum generating device may be eliminated and energy consumption may therefore be eliminated or reduced, and a battery may be omitted or a smaller battery may be used. As a result, production costs may be reduced and a device better suited as a single-use device may be accomplished.

In an embodiment, the at least one initially pre-evacuated vacuum container is connected to a vacuum valve having a valve membrane, and the valve system includes a hollow vacuum needle having a needle tip adapted to penetrate the valve membrane of said vacuum valve. Thereby, when suction pressure is needed for taking a tissue sample, the tip of the hollow vacuum needle may penetrate the valve membrane of said vacuum valve. It is also possible that, between sampling operations, when no suction pressure is needed to take tissue samples, by retracting the hollow vacuum needle from the valve membrane, the valve membrane of the vacuum valve may be used to close tightly and ensure that the remaining vacuum in the initially pre-evacuated vacuum container is preserved. Alternatively, a separate valve may be used for this purpose and the hollow vacuum needle may remain inserted into the membrane between sampling operations.

In an embodiment, the vacuum source has the form of a number of initially pre-evacuated vacuum containers, and the valve system is adapted to connect each initially pre-evacuated vacuum container separately and in succession, corresponding to the respective consecutive sampling operations, with the vacuum channel in the biopsy needle. Thereby, it may be ensured that a consistent suction pressure is applied in the tissue compartment of the inner sample needle at each consecutive sampling operation, because a new initially pre-evacuated vacuum container is used for every sampling operation. In this way, the suction pressure supplied by the vacuum source is not reduced at every sampling operation. According to this embodiment, each initially pre-evacuated vacuum container may be connected with the vacuum channel in the biopsy needle by means of a manifold incorporating a separate valve for each initially pre-evacuated vacuum container. However, preferably, each initially pre-evacuated vacuum container is sealed by a previously unbroken membrane to be penetrated by the tip of a hollow vacuum needle, as explained above, in order to connect the respective container with the vacuum channel in the biopsy needle. In this way, leakage of the initially pre-evacuated vacuum containers may be minimised or avoided during storage, thereby maximising shelf life of the product.

In an embodiment, each initially pre-evacuated vacuum container is connected to a respective vacuum valve having a valve membrane, and the valve system includes a hollow vacuum needle having a needle tip adapted to penetrate the valve membrane of each vacuum valve and an opposed connector end connected to the vacuum channel in the biopsy needle. Thereby, because each initially pre-evacuated vacuum container may be sealed by a previously unbroken membrane, as explained above, leakage of the initially pre-evacuated vacuum containers may be minimised or avoided during storage, thereby maximising shelf life of the product.

In a structurally particularly advantageous embodiment, the respective vacuum valves are arranged along a path, such as a circular arc or a circle, and the arrangement of the valves and the needle tip of the hollow vacuum needle are relatively displaceable so that the needle tip is positionable at each vacuum valve.

In an embodiment, the vacuum source has the form of a number of initially pre-evacuated vacuum containers formed in a common housing. Thereby, by arranging the different vacuum containers in an integral construction, a relatively rigid construction suitably holding the vacuum pressure may be achieved with less material than if separate vacuum containers were used.

In a structurally particularly advantageous embodiment, the common housing has the form of a cylindrical container separated into the initially pre-evacuated vacuum containers by means of internally extending partition walls.

In a structurally particularly advantageous embodiment, the vacuum source has the form of a cylindrical container separated into a number of initially pre-evacuated vacuum containers by means of internally extending partition walls, the respective vacuum valves are arranged on an end wall of the cylindrical container, the cylindrical container is arranged rotatably about its central axis, and the needle tip of the hollow vacuum needle is arranged at a fixed position in the rotational direction of the cylindrical container. Thereby, by stepwise rotation of the cylindrical container, the needle tip of the hollow vacuum needle may be located at each vacuum valve, one-by-one. At each vacuum valve, by displacement of the hollow vacuum needle in its longitudinal direction relative to the cylindrical container, the needle tip may penetrate the membrane of the vacuum valve, whereby a suction pressure may by achieved in the tissue compartment of the inner sample needle.

In an alternative embodiment, the vacuum source has the form of a number of initially pre-evacuated vacuum containers formed in a common housing, the respective vacuum valves are arranged at the common housing along a circular arc, and the needle tip of the hollow vacuum needle is arranged on a swing arm so that the needle tip is positionable at each vacuum valve. Thereby, by suitable arrangement of the respective vacuum valves, the needle tip may be positionable at each vacuum valve by relatively little rotation of the swing arm.

In an alternative embodiment, the vacuum source has the form of a single initially pre-evacuated vacuum container connected with the vacuum channel in the biopsy needle by means of a valve, and the biopsy device is adapted to control the pressure decrease in the tissue compartment of the inner sample needle by means of the valve. Thereby, a simple vacuum container having only one single internal chamber may be employed by using the valve in order to supply a dose of the initial vacuum of the single initially pre-evacuated vacuum container at each one of the limited number of consecutive sampling operations.

In an alternative embodiment, the vacuum source has the form of a single initially pre-evacuated vacuum container connected with a vacuum dispensing reservoir by means of a first valve, and the vacuum dispensing reservoir is connected with the vacuum channel in the biopsy needle by means of a second valve. Thereby, a simple vacuum container having only one single internal chamber may be employed. By means of the vacuum dispensing reservoir, the initial vacuum of the single initially pre-evacuated vacuum container may be dosed at each one of the limited number of consecutive sampling operations. At each sampling operation, firstly, the first valve is opened while the second valve is maintained closed in order to evacuate the vacuum dispensing reservoir. Subsequently, the second valve is opened while the first valve is maintained closed in order to provide a pressure decrease in the tissue compartment of the inner sample needle. In this way, by means of the vacuum dispensing reservoir, the initial vacuum of the single initially pre-evacuated vacuum container may be dosed more consistently.

In an embodiment, the single initially pre-evacuated vacuum container is connected to a vacuum valve having a valve membrane, and the valve system includes a hollow vacuum needle having a needle tip adapted to penetrate the valve membrane of the vacuum valve and an opposed connector end connected to the first valve. Thereby, when suction pressure is needed for taking a tissue sample, the tip of the hollow vacuum needle may penetrate the valve membrane of said vacuum valve, and between sampling operations, when no suction pressure is needed to take tissue samples, the valve membrane of the vacuum valve may close tightly and ensure that the remaining vacuum in the initially pre-evacuated vacuum container is even better preserved.

In an embodiment, the biopsy device is a handheld biopsy device, and the at least one initially pre-evacuated vacuum container is arranged in the housing of the biopsy device.

The invention will now be explained in more detail below by means of examples of embodiments with reference to the very schematic drawing, in which.

Figure 1:
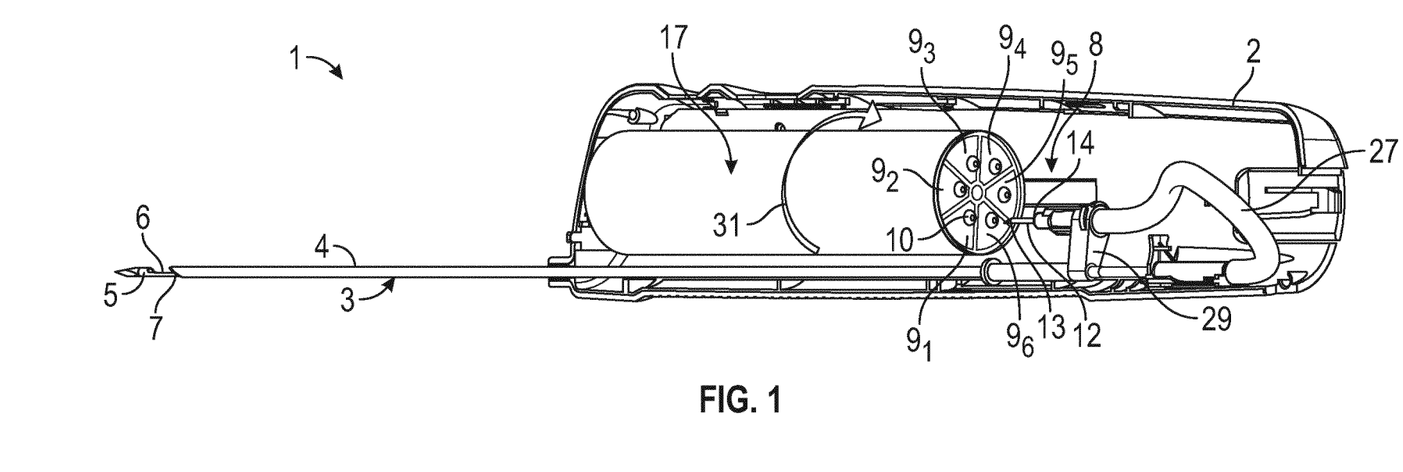
FIG. 1 is a perspective view of a biopsy device according to the invention, wherein part of the housing has been removed, and wherein a hollow vacuum needle is in a first position.
Figure 2:
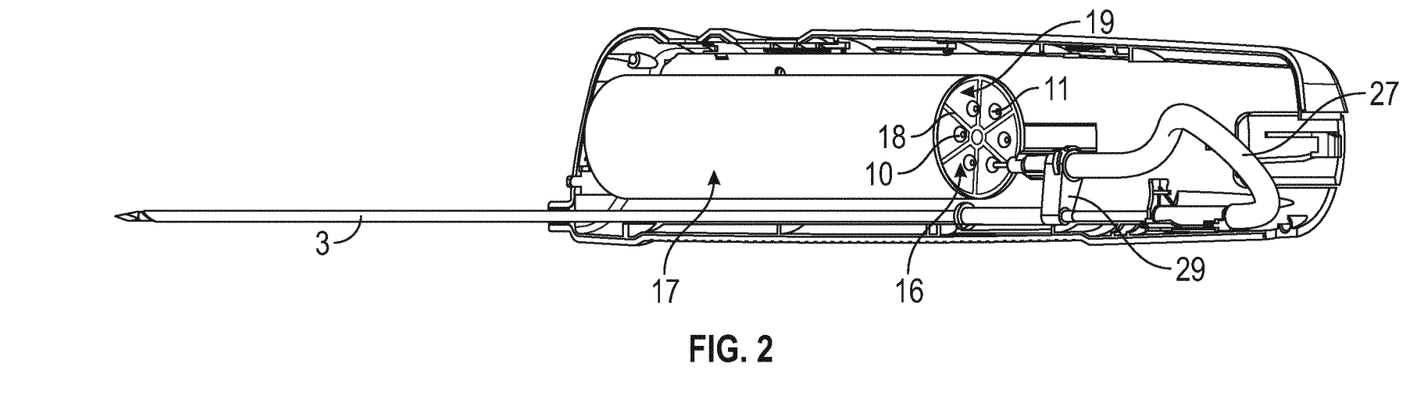
FIG. 2 is a perspective view corresponding to that of FIG. 1, wherein the hollow vacuum needle is in a second position.

FIGS. 1 and 2 illustrate an embodiment of a biopsy device 1 according to the present invention. The biopsy device 1 includes a housing 2 and a biopsy needle 3 extending from the housing and being adapted for insertion into the tissue of a patient. The biopsy needle 3 includes an outer cutting needle 4 and an inner sample needle 5 with a tissue compartment 6 for receiving a tissue sample. The outer cutting needle 4 surrounds the inner sample needle 5, and the outer cutting needle 4 and the inner sample needle 5 are arranged slidingly in relation to each other along their longitudinal direction. The outer cutting needle 4 has a cutting end 7 distant from the housing 2 adapted to cut and separate a tissue sample located in the tissue compartment 6 of inner sample needle 5 from the surrounding body tissue of a patient. The biopsy device 1 is furthermore adapted to, during each sampling operation whereby a tissue sample is collected in the tissue compartment 6 of the inner sample needle 5, displace the outer cutting needle 4 and the inner sample needle 5 at least between an open position of the tissue compartment 6 as illustrated in FIG. 1 in which the tissue compartment 6 extends beyond the cutting end 7 of the outer cutting needle 4 and a closed position of the tissue compartment 6 as illustrated in FIG. 2 in which the outer cutting needle 4 covers the tissue compartment 6. Thereby, when the biopsy needle has been inserted into the tissue of the patient, when the tissue compartment 6 is brought from its open position to its closed position, the tissue sample located in the tissue compartment 6 is cut free from the surrounding tissue of the patient by means of the cutting end 7 of the outer cutting needle 4.

The biopsy device 1 includes a vacuum source for providing a pressure decrease in the tissue compartment 6 of the inner sample needle 5 via a not shown vacuum channel arranged longitudinally in the biopsy needle 3. The not shown vacuum channel may typically be arranged in the inner sample needle 5 and preferably along the centre line of the inner sample needle 5. The biopsy device 1 furthermore includes a valve system 8 adapted to provide a pressure decrease in the tissue compartment 6 at each sampling operation. The pressure decrease may be provided in the tissue compartment 6 before, during or after that the tissue compartment is brought to its open position. Thereby, an at least partial vacuum may be created in the tissue compartment whereby the tissue sample may be drawn into the tissue compartment during the cutting action of the outer cutting needle 4. Thereby, the taking of tissue samples may be facilitated and larger tissue samples may be obtained.

According to the present invention, the vacuum source has the form of at least one initially pre-evacuated vacuum container $9_1$, $9_2$, $9_3$, $9_4$, $9_5$, $9_6$, 21, and the biopsy device 1 is adapted to, by means of the initial vacuum of the at least one initially pre-evacuated vacuum container, provide a pressure decrease in the tissue compartment 6 of the inner sample needle 5 at each one of a limited number of consecutive sampling operations. As it will be explained in the following, this may be achieved by different embodiments of the invention. The biopsy device 1 may thereby be well suited as a single-use device, whereby the device may be delivered with the at least one initially pre-evacuated vacuum container which may be used up during said limited number of consecutive sampling operations. Thereby, the need for an electric motor for driving a vacuum generating device may be eliminated and energy consumption may therefore be eliminated or reduced, a battery may be omitted or a smaller battery may be used. As a result, production costs may be reduced. In the illustrated embodiments, the at least one initially pre-evacuated vacuum container $9_1$, $9_2$, $9_3$, $9_4$, $9_5$, $9_6$, 21, is arranged in the housing 2 of the biopsy device 1 and the biopsy device 1 is a handheld biopsy device 1.

In the embodiments of the invention illustrated in FIGS. 1 to 8, the at least one initially pre-evacuated vacuum container $9_1$, $9_2$, $9_3$, $9_4$, $9_5$, $9_6$, 21 is in fluid connection with a vacuum valve 10 having a valve membrane 11, and the valve system 8 includes a hollow vacuum needle 12 having a needle tip 13 adapted to penetrate the valve membrane 11 of said vacuum valve 10. In said embodiments, this is done by displacement of the hollow vacuum needle 12 in its longitudinal direction in the housing, whereby the vacuum valve or valves 10 is/are fixed against displacement in this direction. As seen, in said embodiments, the vacuum valve or valves 10 is/are arranged directly on the at least one initially pre-evacuated vacuum container. Alternatively, the needle could be fixed in its longitudinal direction and the vacuum valve or valves 10 could be displaced in order for the hollow vacuum needle 12 to penetrate the valve membrane 11 of the valve or valves 10. When suction pressure is needed for taking a tissue sample, the tip of the hollow vacuum needle 12 may penetrate the valve membrane 11 of said vacuum valve 10, and before use, the valve membrane 11 may close tightly and ensure that the vacuum in the initially pre-evacuated vacuum container is preserved.

In the embodiments of the invention illustrated in FIGS. 1 to 7, the vacuum source has the form of six initially pre-evacuated vacuum containers $9_1$, $9_2$, $9_3$, $9_4$, $9_5$, $9_6$, and the valve system 8 is adapted to connect each initially pre-evacuated vacuum container separately and in succession, corresponding to the respective consecutive sampling operations, with the not shown vacuum channel in the biopsy needle 3. Any suitable number of initially pre-evacuated vacuum containers may of course be employed. Each initially pre-evacuated vacuum container $9_1$, $9_2$, $9_3$, $9_4$, $9_5$, $9_6$ is connected to a respective vacuum valve 10 having a valve membrane 11, and the valve system 8 includes a hollow vacuum needle 12 having a needle tip 13 adapted to penetrate the valve membrane 11 of each vacuum valve 10 and an opposed connector end 14 connected to the not shown vacuum channel in the biopsy needle 3.

Figure 5:
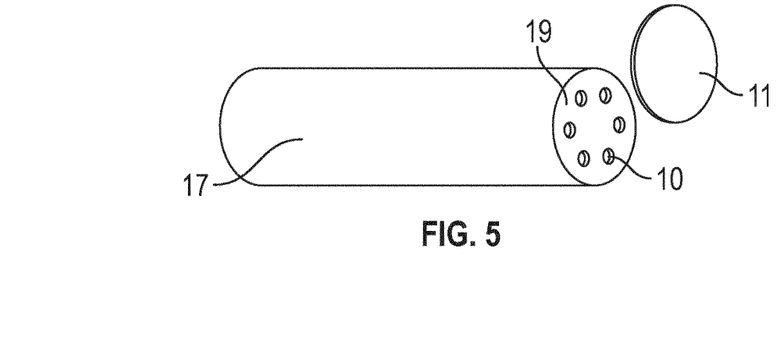
FIG. 5 is a perspective view of an initially pre-evacuated vacuum container of the biopsy device of FIGS. 3 and 4, wherein a valve membrane has been removed.
Figure 6:
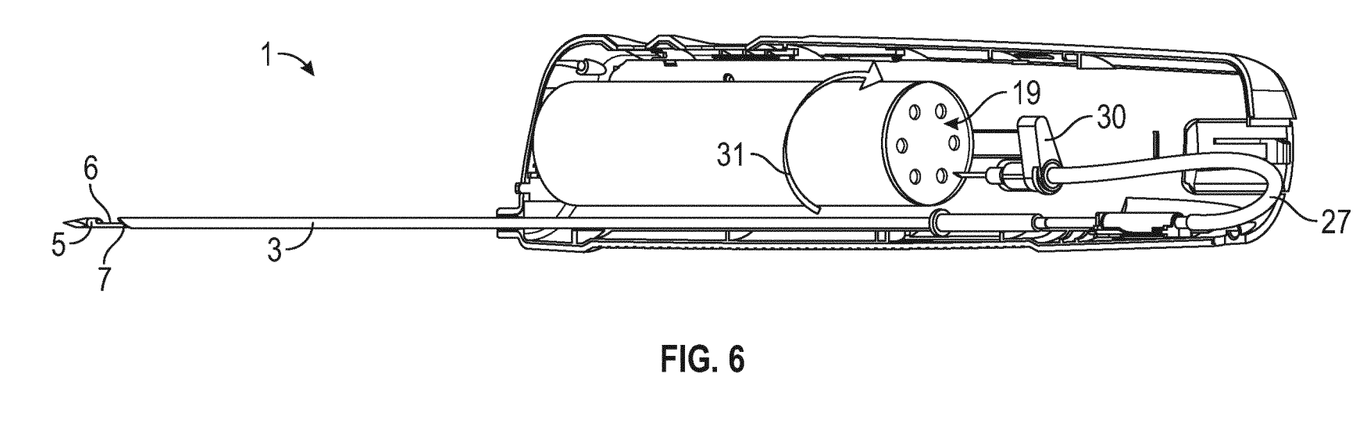
FIG. 6 is a perspective view corresponding to that of FIG. 3 of another embodiment of the biopsy device according to the invention.
Figure 7:
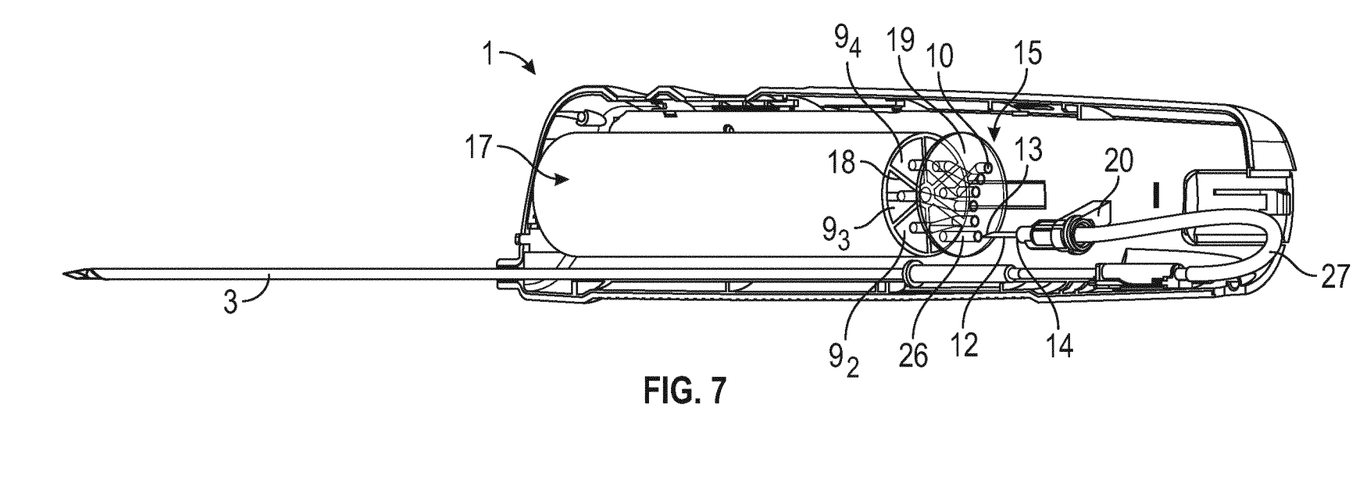
FIG. 7 is a perspective view of yet another embodiment of the biopsy device according to the invention.

As seen, in the embodiments of the invention illustrated in FIGS. 1 to 7, the respective vacuum valves 10 are arranged along a path in the form of a circle 16 in FIGS. 1 to 6 and in the form of a circular arc 15 in FIG. 7, and the arrangement of the valves 10 and the needle tip 13 of the hollow vacuum needle 12 are relatively displaceable so that the needle tip 13 is positionable at each vacuum valve 10.

Furthermore, it is seen that in the embodiments illustrated in FIGS. 1 to 7, a common housing in the form of a cylindrical container 17 is separated into the initially pre-evacuated vacuum containers $9_1$, $9_2$, $9_3$, $9_4$, $9_5$, $9_6$ by means of internally extending partition walls 18. As seen, the internally extending partition walls 18 extend radially in the cylindrical container 17 whereby a symmetric arrangement may be obtained. Thereby, the pressure resistance of the cylindrical container 17 may be optimised. However, the internally extending partition walls 18 may be arranged in other ways; for instance they may have a curved configuration. The internally extending partition walls 18 may also be arranged spaced in the longitudinal direction of the cylindrical container 17. Furthermore, the common housing formed by the initially pre-evacuated vacuum containers need not be cylindrical, but may have any suitable form.

In the embodiments of the invention illustrated in FIGS. 1 to 6, the respective vacuum valves 10 are arranged on an end wall 19 of the cylindrical container 17, the cylindrical container 17 is arranged rotatably about its central axis as illustrated by the arrow 31, and the needle tip 13 of the hollow vacuum needle 12 is arranged at a fixed position in the rotational direction of the cylindrical container 17. Thereby, by rotation of the cylindrical container 17, the arrangement of the valves 10 and the needle tip 13 of the hollow vacuum needle 12 are relatively displaceable so that the needle tip 13 is positionable at each vacuum valve 10.

In an alternative embodiment of the invention illustrated in FIG. 7, the respective vacuum valves 10 are arranged at the common housing along a circular arc 15, and the needle tip 13 of the hollow vacuum needle 12 is arranged on a swing arm 20 so that the needle tip 13 is positionable at each vacuum valve 10. An end wall 19 of the cylindrical container 17 and part of the cylindrical container 17 are illustrated as being transparent in order to illustrate connection channels 26 connecting the respective vacuum valves with the corresponding respective initially pre-evacuated vacuum containers $9_1$, $9_2$, $9_3$, $9_4$, $9_5$, $9_6$.

Figure 9:
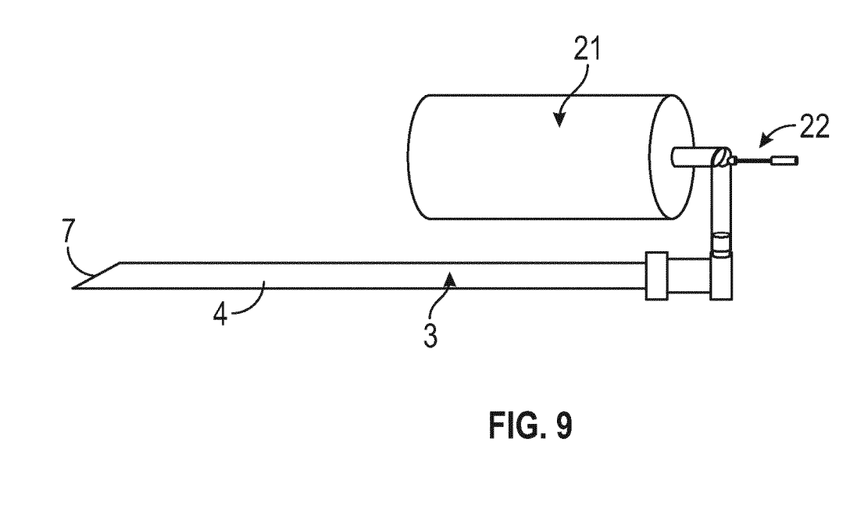
FIGS. 9 and 10 are perspective views of an initially pre-evacuated vacuum container and biopsy needle of two different embodiments of the biopsy device according to the invention.
Figure 10:
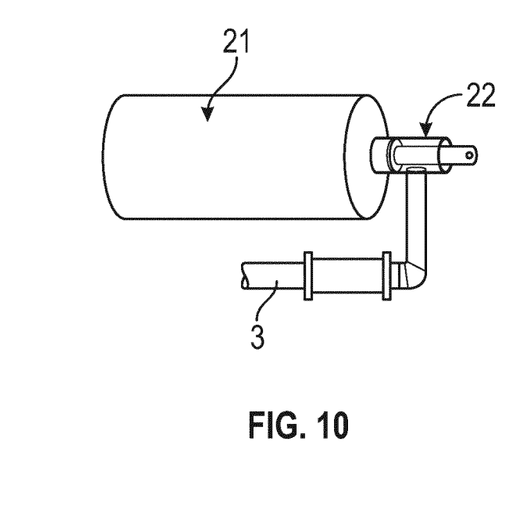

In the alternative embodiments of the invention illustrated in FIGS. 9 and 10, the vacuum source has the form of a single initially pre-evacuated vacuum container 21 connected with the not shown vacuum channel in the biopsy needle 3 by means of a valve 22, and the biopsy device 1 is adapted to control the pressure decrease in the tissue compartment 6 of the inner sample needle 5 by means of the valve 22. The valve 22 may for instance be a pressure control valve or an on/off valve. The pressure decrease in the tissue compartment 6 may be so to say be dosed correctly by means of controlling the opening time and closing time of the valve, and possibly how much the valve is opened. As seen, in FIG. 9, a butterfly valve is used, whereas in FIG. 10, a piston valve is used.

Figure 8:
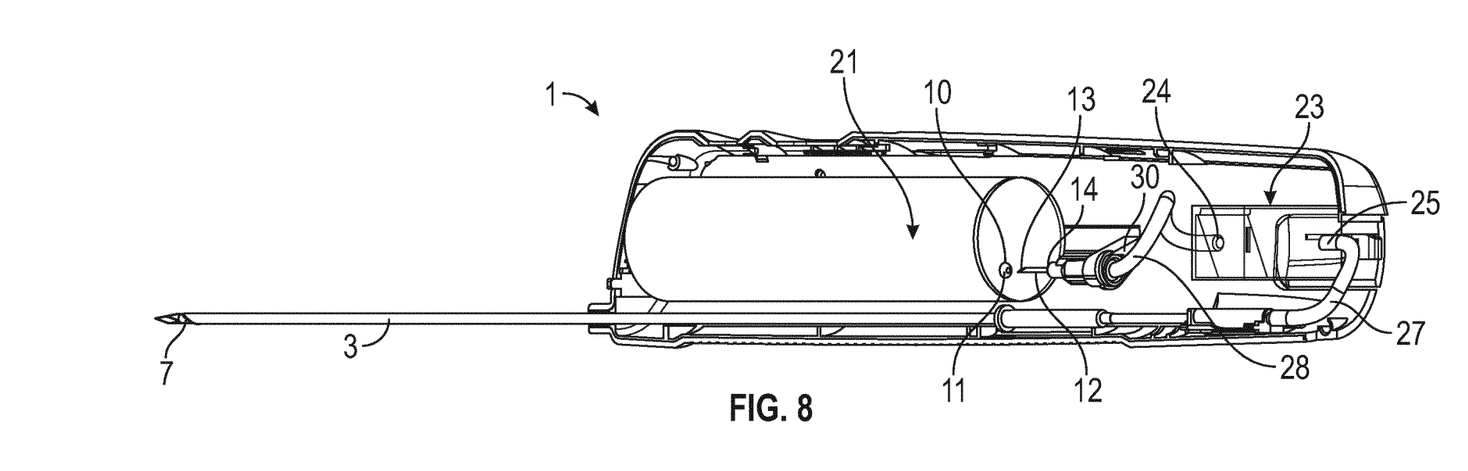
FIG. 8 is a perspective view of yet another embodiment of the biopsy device according to the invention.

In an alternative embodiment of the invention illustrated in FIG. 8, the vacuum source has the form of a single initially pre-evacuated vacuum container 21 connected with a vacuum dispensing reservoir 23 by means of a first valve 24, and the vacuum dispensing reservoir 23 is connected with the not shown vacuum channel in the biopsy needle 3 by means of a second valve 25. The second valve 25 is connected with the not shown vacuum channel in the biopsy needle 3 by means of a vacuum connection tube 27. By means of the vacuum dispensing reservoir 23, the initial vacuum of the single initially pre-evacuated vacuum container 21 may be dosed at each one of the limited number of consecutive sampling operations. At each sampling operation, firstly, the first valve 24 is opened while the second valve 25 is maintained closed in order to evacuate the vacuum dispensing reservoir 23. Subsequently, the second valve 25 is opened while the first valve 24 is maintained closed in order to provide a pressure decrease in the tissue compartment 6 of the inner sample needle 5. In this way, by means of the vacuum dispensing reservoir 23, the initial vacuum of the single initially pre-evacuated vacuum container 21 may be dosed more consistently. If desired, the first valve 24 may be controlled so that it opens for a longer period of time for each new sample to be taken, whereby the actual pressure obtained in the vacuum dispensing reservoir 23 is approximately the same for each sample operation.

In the embodiment of the invention illustrated in FIG. 8, optionally, as illustrated, the single initially pre-evacuated vacuum container 21 is provided with a vacuum valve 10 having a valve membrane 11, and the valve system 8 includes a hollow vacuum needle 12 having a needle tip 13 adapted to penetrate the valve membrane 11 of the vacuum valve 10 and an opposed connector end 14 connected to the first valve 24. The first valve 24 is connected with the connector end 14 of the hollow vacuum needle 12 by means of a flexible vacuum connection tube 28. Thereby, when suction pressure is needed for taking a tissue sample, the needle tip 13 of the hollow vacuum needle 12 may penetrate the valve membrane 11 of said vacuum valve 10, and between sampling operations, when no suction pressure is needed to take tissue samples, the needle tip 13 of the hollow vacuum needle 12 may be retracted from the valve membrane 11, and the valve membrane 11 of the vacuum valve 10 may close tightly and ensure that the remaining vacuum in the initially pre-evacuated vacuum container 21 is even better preserved. Preferably, however, the hollow vacuum needle 12 may be inserted into the valve membrane 11 at the beginning of the operation of the biopsy device and may remain inserted into the valve membrane 11 during consecutive sampling operations, and the first valve 24 may be controlled to close between sampling operations. The main advantage of the combination of the hollow vacuum needle 12 and the valve membrane 11 may be that a tight closure may be provided during storage of the biopsy device before bringing it into use.

Alternatively, in the embodiment of the invention illustrated in FIG. 8, if the vacuum valve 10 with the hollow vacuum needle 12 is omitted, the first valve 24 may be connected directly with the single initially pre-evacuated vacuum container 21 by means of the flexible vacuum connection tube 28. The first valve 24 may be fully functional and sufficient for opening and closing the connection between the single initially pre-evacuated vacuum container 21 and the vacuum dispensing reservoir 23. However, as mentioned above, and depending on the art of the first valve 24, the further addition of the vacuum valve 10 and the hollow vacuum needle 12 may provide even better closure during longer periods of time, such as storage time.

Alternatively, in the embodiment of the invention illustrated in FIG. 8, the vacuum valve with the hollow vacuum needle 12 may replace or constitute the first valve 24 so that the connector end 14 of the hollow vacuum needle 12 may be connected directly with the vacuum dispensing reservoir 23 by means of the flexible vacuum connection tube 28.

Figure 3:
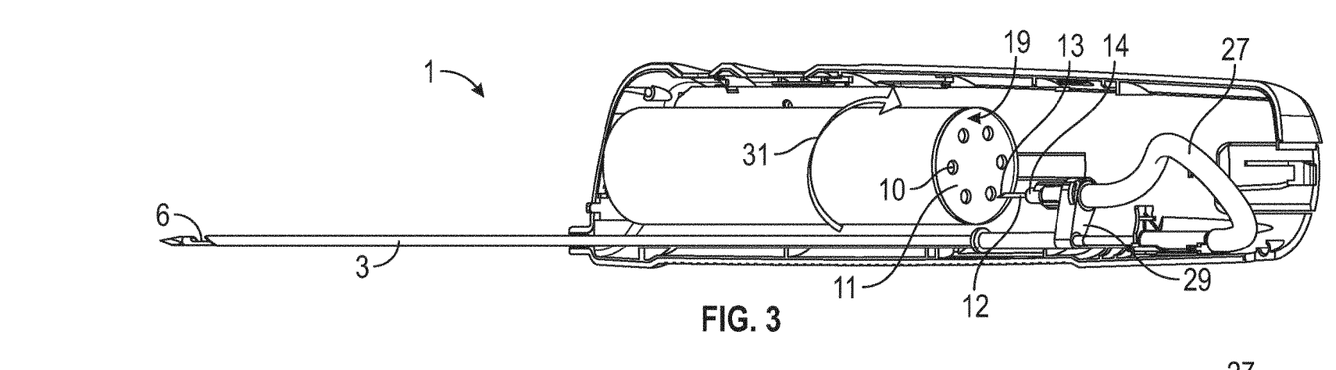
FIGS. 3 and 4 are perspective views corresponding to those of FIGS. 1 and 2, respectively, of another embodiment of the biopsy device according to the invention.
Figure 4:
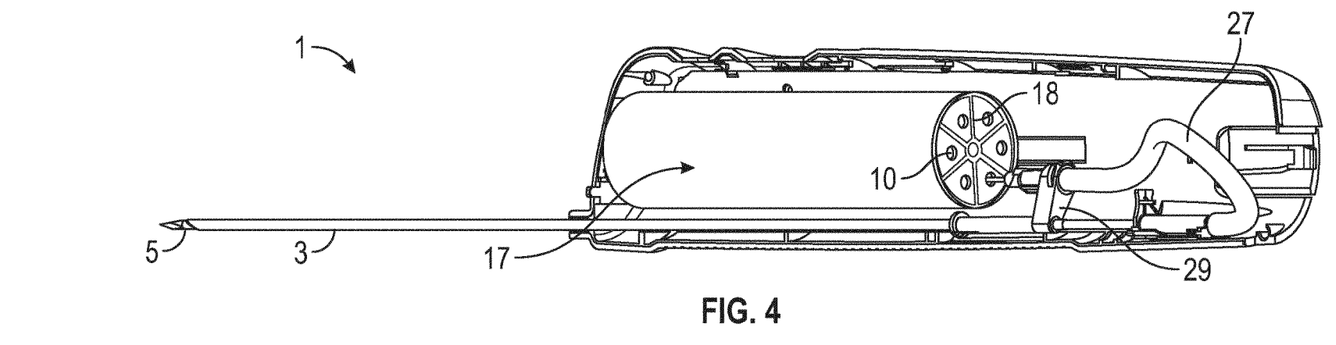

It is noted that in the embodiment illustrated in FIGS. 1 and 2, each vacuum valve 10 is provided with a separate valve membrane 11 arranged in or at a respective hole in the end wall 19 of the cylindrical container 17 forming the initially pre-evacuated vacuum containers. In FIGS. 1 and 2, the end wall 19 is illustrated as being transparent in order to illustrate the internally extending partition walls 18 of the cylindrical container 17. It is furthermore noted that in the embodiments illustrated in FIGS. 3 to 6, all six vacuum valves 10 are provided with a common valve membrane 11 as illustrated in FIG. 5. The common valve membrane 11 is placed on the outside or inside of the end wall 19 of the cylindrical container 17 and is sealingly connected with the end wall 19. Each vacuum valve 10 is formed as a hole in the end wall 19 so that the hollow vacuum needle 12 may enter the corresponding initially pre-evacuated vacuum container 9 by penetrating the membrane at said hole. In FIGS. 3 and 6, the common valve membrane 11 is placed on the outside of the end wall 19, but the membrane is illustrated as being transparent. In FIG. 4 illustrating the same embodiment as FIG. 3, both the membrane 11 and the end wall 19 are illustrated as being transparent in order to illustrate the internally extending partition walls 18 of cylindrical container 17.

The valve membrane 11 may have the form of a self-sealing diaphragm or membrane formed of a suitable self-sealing elastomeric material which can be readily penetrated by a conventional surgical needle or the like. As seen, in the embodiments illustrated in FIGS. 3 to 6, the common valve membrane 11 is a flat piece of material, and this may also be the case in the embodiment illustrated in FIGS. 1 and 2 in which each valve 10 is provided with a separate valve membrane 11. However, in this latter embodiment, each separate valve membrane 11 has a mushroom-like form having a rounded head which is visible in the figures. The rounded head has a diameter slightly larger than the corresponding hole in the end wall 19 of the cylindrical container 17, and a not visible stem is arranged below the rounded head and is inserted into said hole in the end wall 19. Thereby, because the cylindrical container 17 is evacuated, the rounded head of the mushroom-formed valve membrane 11 is tightly held onto the outside of said hole and thereby tightly closes the hole. The stem of the rounded head serves to keep the mushroom-formed valve membrane 11 at place at the hole. As it is also seen in FIGS. 1 and 2, the rounded head is provided with a small central depression which serves to steer the needle tip 13 of the hollow vacuum needle 12 to penetrate the mushroom-formed valve membrane 11 at its centre. However, according to the present invention, the valve membrane 11 may have many different configurations, such as for instance a small tube with an integrated end wall to be penetrated by the hollow vacuum needle 12.

In the embodiments illustrated in FIGS. 7 to 10, the initially pre-evacuated vacuum container 9 is not adapted to be rotated during sampling, and therefore the initially pre-evacuated vacuum container may have a form that fits the internal geometry of the housing 2 of the biopsy device 1, independently of the form of the housing, thereby making good use of the available space within the housing.

It is further noted that in the embodiment illustrated in FIGS. 1 and 2 and in the embodiment illustrated in FIGS. 3 and 4, the longitudinal displacement of the hollow vacuum needle 12 is coupled to the longitudinal displacement of the outer cutting needle 4 of biopsy needle 3 by means of a connecting arm 29 so that the hollow vacuum needle 12 may penetrate the valve membrane 11 of the respective vacuum valve 10 in a timed manner in relation to the point in time when the cutting end 7 of the outer cutting needle 4 starts to cut the tissue and close the tissue compartment 6 of inner sample needle 5. For instance, the penetration of the valve membrane 11 may be arranged to occur before, during or after opening of the tissue compartment 6, and subsequently, the tissue may be cut. Thereby, in a simple manner, the application of the pressure decrease in the tissue compartment 6 may be timed advantageously so that the taking of the tissue sample is vacuum-assisted when cutting the tissue sample from the surrounding tissue. In the embodiments illustrated in FIGS. 6, 7 and 8, on the other hand, a needle holding arm 30 and the swing arm 20, respectively holding the hollow vacuum needle 12, are not directly coupled to the outer cutting needle 4. Therefore, according to these embodiments, the longitudinal movement of the hollow vacuum needle 12 is controlled independently from the longitudinal movement of the outer cutting needle 4.

According to the present invention, by an initially pre-evacuated vacuum container is understood a vacuum container which has been evacuated before taking the biopsy device into use. When the biopsy device according to the invention is taken into use, a number of consecutive tissue samples may be taken before the vacuum of the pre-evacuated vacuum container has so to say been used up and no more tissue samples may be taken, assisted by means of vacuum. Suitably, the at least one initially pre-evacuated vacuum container may be pre-evacuated to 0,5-0,05 bar (abs). Preferably, the at least one initially pre-evacuated vacuum container may be pre-evacuated to 0,4 bar (abs) or less. More preferred, the at least one initially pre-evacuated vacuum container may be pre-evacuated to 0,3 bar (abs) or less. Even more preferred, the at least one initially pre-evacuated vacuum container may be pre-evacuated to 0,2 bar (abs) or less.

The biopsy device according to the present invention is preferably a single use product, i.e. the biopsy device is intended for taking a sequence of tissue samples from a patient and for subsequently being discarded.

According to the present invention, the following embodiments are disclosed:

Embodiment 1: A biopsy device (1) including a housing (2) and a biopsy needle (3) extending from the housing, the biopsy needle (3) including an outer cutting needle (4) and an inner sample needle (5) with a tissue compartment (6) for receiving a tissue sample, the outer cutting needle (4) surrounding the inner sample needle (5), the outer cutting needle (4) and the inner sample needle (5) being arranged slidingly in relation to each other along their longitudinal direction, the outer cutting needle (4) having a cutting end (7) distant from the housing (2), the biopsy device (1) being adapted to, during each sampling operation whereby a tissue sample is collected in the tissue compartment (6) of the inner sample needle (5), displace the outer cutting needle (4) and the inner sample needle (5) at least between an open position of the tissue compartment (6) in which the tissue compartment (6) extends beyond the cutting end (7) of the outer cutting needle (4) and a closed position of the tissue compartment (6) in which the outer cutting needle (4) covers the tissue compartment (6), the biopsy device (1) including a vacuum source for providing a pressure decrease in the tissue compartment (6) of the inner sample needle (5) via a vacuum channel arranged longitudinally in the biopsy needle (3), and the biopsy device (1) including a valve system (8) adapted to provide a pressure decrease in the tissue compartment (6) at each sampling operation, characterised in that the vacuum source has the form of at least one initially pre-evacuated vacuum container ($9_1$, $9_2$, $9_3$, $9_4$, $9_5$, $9_6$, 21), and in that the biopsy device (1) is adapted to, by means of the initial vacuum of the at least one initially pre-evacuated vacuum container (9), provide a pressure decrease in the tissue compartment (6) of the inner sample needle (5) at each one of a limited number of consecutive sampling operations.

Embodiment 2: A biopsy device according to embodiment 1, wherein the at least one initially pre-evacuated vacuum container ($9_1$, $9_2$, $9_3$, $9_4$, $9_5$, $9_6$, 21) is connected to a vacuum valve (10) having a valve membrane (11), and wherein the valve system (8) includes a hollow vacuum needle (12) having a needle tip (13) adapted to penetrate the valve membrane (11) of said vacuum valve (10).

Embodiment 3: A biopsy device according to embodiment 1 or 2, wherein the vacuum source has the form of a number of initially pre-evacuated vacuum containers ($9_1$, $9_2$, $9_3$, $9_4$, $9_5$, $9_6$), and wherein the valve system (8) is adapted to connect each initially pre-evacuated vacuum container separately and in succession, corresponding to the respective consecutive sampling operations, with the vacuum channel in the biopsy needle (3).

Embodiment 4: A biopsy device according to embodiment 3, wherein each initially pre-evacuated vacuum container ($9_1$, $9_2$, $9_3$, $9_4$, $9_5$, $9_6$) is connected to a respective vacuum valve (10) having a valve membrane (11), and wherein the valve system (8) includes a hollow vacuum needle (12) having a needle tip (13) adapted to penetrate the valve membrane (11) of each vacuum valve (10) and an opposed connector end (14) connected to the vacuum channel in the biopsy needle (3).

Embodiment 5: A biopsy device according to embodiment 4, wherein the respective vacuum valves (10) are arranged along a path, such as a circular arc (15) or a circle (16), and wherein the arrangement of the valves (10) and the needle tip (13) of the hollow vacuum needle (12) are relatively displaceable so that the needle tip (13) is positionable at each vacuum valve (10).

Embodiment 6: A biopsy device according to any one of the preceding embodiments, wherein the vacuum source has the form of a number of initially pre-evacuated vacuum containers ($9_1$, $9_2$, $9_3$, $9_4$, $9_5$, $9_6$) formed in a common housing.

Embodiment 7: A biopsy device according to embodiment 6, wherein the common housing has the form of a cylindrical container (17) separated into the initially pre-evacuated vacuum containers ($9_1$, $9_2$, $9_3$, $9_4$, $9_5$, $9_6$) by means of internally extending partition walls (18).

Embodiment 8: A biopsy device according to embodiment 4 or 5, wherein the vacuum source has the form of a cylindrical container (17) separated into a number of initially pre-evacuated vacuum containers ($9_1$, $9_2$, $9_3$, $9_4$, $9_5$, $9_6$) by means of internally extending partition walls (18), wherein the respective vacuum valves (10) are arranged on an end wall (19) of the cylindrical container (17), wherein the cylindrical container (17) is arranged rotatably about its central axis, and wherein the needle tip (13) of the hollow vacuum needle (12) is arranged at a fixed position in the rotational direction of the cylindrical container (17).

Embodiment 9: A biopsy device according to embodiment 4, wherein the vacuum source has the form of a number of initially pre-evacuated vacuum containers ($9_1$, $9_2$, $9_3$, $9_4$, $9_5$, $9_6$) formed in a common housing, wherein the respective vacuum valves (10) are arranged at the common housing along a circular arc (15), and wherein the needle tip (13) of the hollow vacuum needle (12) is arranged on a swing arm (20) so that the needle tip (13) is positionable at each vacuum valve (10).

Embodiment 10: A biopsy device according to embodiment 1, wherein the vacuum source has the form of a single initially pre-evacuated vacuum container (21) connected with the vacuum channel in the biopsy needle by means of a valve (22), and wherein the biopsy device (1) is adapted to control the pressure decrease in the tissue compartment (6) of the inner sample needle (5) by means of the valve (22).

Embodiment 11: A biopsy device according to embodiment 1, wherein the vacuum source has the form of a single initially pre-evacuated vacuum container (21) connected with a vacuum dispensing reservoir (23) by means of a first valve (24), and wherein the vacuum dispensing reservoir (23) is connected with the vacuum channel in the biopsy needle (3) by means of a second valve (25).

Embodiment 12: A biopsy device according to embodiment 11, wherein the single initially pre-evacuated vacuum container (21) is connected to a vacuum valve (10) having a valve membrane (11), and wherein the valve system (8) includes a hollow vacuum needle (12) having a needle tip (13) adapted to penetrate the valve membrane (11) of the vacuum valve (10) and an opposed connector end (14) connected to the first valve (24).

Embodiment 13: A biopsy device according to any one of the preceding embodiment, wherein the biopsy device (1) is a handheld biopsy device, and wherein the at least one initially pre-evacuated vacuum container ($9_1$, $9_2$, $9_3$, $9_4$, $9_5$, $9_6$, 21) is arranged in the housing (2) of the biopsy device (1).

LIST OF REFERENCE NUMBERS 1 biopsy device
2 housing of biopsy device
3 biopsy needle
4 outer cutting needle of biopsy needle
5 inner sample needle of biopsy needle
6 tissue compartment of inner sample needle
7 cutting end of outer cutting needle
8 valve system
9 initially pre-evacuated vacuum container
10 vacuum valve
11 valve membrane of vacuum valve
12 hollow vacuum needle
13 needle tip of hollow vacuum needle
14 connector end of hollow vacuum needle
15 circular arc of arrangement of vacuum valves
16 circle of arrangement of vacuum valves
17 cylindrical container
18 internally extending partition walls of cylindrical container
19 end wall of cylindrical container
20 swing arm 21 initially pre-evacuated vacuum container
22 valve
23 vacuum dispensing reservoir
24 first valve
25 second valve
26 connection channel
27, 28 vacuum connection tube
29 connecting arm
30 needle holding arm
31 arrow indicating rotation

The invention claimed is:

1. A biopsy device comprising:
a housing; and
a biopsy needle extending from the housing, the biopsy needle including an outer cutting needle and an inner sample needle with a tissue compartment for receiving a tissue sample, the outer cutting needle surrounding the inner sample needle, the outer cutting needle and the inner sample needle being arranged slidingly in relation to each other along their longitudinal direction, the outer cutting needle having a cutting end distant from the housing, and
wherein the biopsy device is adapted to, during a sampling operation whereby a tissue sample is collected in the tissue compartment of the inner sample needle, displace the outer cutting needle and the inner sample needle at least between an open position of the tissue compartment in which the tissue compartment extends beyond the cutting end of the outer cutting needle and a closed position of the tissue compartment in which the outer cutting needle covers the tissue compartment,
wherein the biopsy device includes a vacuum source for providing a pressure decrease in the tissue compartment of the inner sample needle via a vacuum channel arranged longitudinally in the biopsy needle, and
wherein the biopsy device includes a valve system adapted to provide a pressure decrease in the tissue compartment during the sampling operation, wherein the vacuum source includes a number of initially pre-evacuated vacuum containers, in that the biopsy device is adapted to, by use of a vacuum of the number of initially pre-evacuated vacuum containers, provide a pressure decrease in the tissue compartment of the inner sample needle during each one of a limited number of consecutive sampling operations, the valve system is adapted to connect each of the number of initially pre-evacuated vacuum containers separately and in succession, corresponding to the respective one of the limited number of consecutive sampling operations, with the vacuum channel in the biopsy needle; and
wherein each of the initially pre-evacuated vacuum containers is connected to a vacuum valve having a valve membrane, and wherein the valve system includes a hollow vacuum needle having a needle tip adapted to penetrate the valve membrane of the vacuum valve.

2. A biopsy device according to claim 1, wherein the valve system further includes an opposed connector end connected to the vacuum channel in the biopsy needle.

3. A biopsy device according to claim 2, wherein the respective vacuum valves are arranged along a curved path, and wherein the arrangement of the valves and the needle tip of the hollow vacuum needle are relatively displaceable so that the needle tip is positionable at each vacuum valve.

4. A biopsy device according to claim 2, wherein the vacuum source includes a cylindrical container separated into the number of initially pre-evacuated vacuum containers via internally extending partition walls, wherein the respective vacuum valves are arranged on an end wall of the cylindrical container, wherein the cylindrical container is arranged rotatably about its central axis, and wherein the needle tip of the hollow vacuum needle is arranged at a fixed position in the rotational direction of the cylindrical container.

5. A biopsy device according to claim 2, wherein the number of initially pre-evacuated vacuum containers are formed in a common housing, wherein the respective vacuum valves are arranged at the common housing along a circular arc, and wherein the needle tip of the hollow vacuum needle is arranged on a swing arm so that the needle tip is positionable at each vacuum valve.

6. A biopsy device according to claim 1, wherein the number of initially pre-evacuated vacuum containers are formed in a common housing.

7. A biopsy device according to claim 6, wherein the common housing is a cylindrical container separated into the initially pre-evacuated vacuum containers via internally extending partition walls.

8. A biopsy device according to claim 1, wherein the biopsy device is a handheld biopsy device, and wherein the at least one initially pre-evacuated vacuum container is arranged in the housing of the biopsy device.

9. A biopsy device comprising:
a housing; and
a biopsy needle extending from the housing, the biopsy needle including an outer cutting needle and an inner sample needle with a tissue compartment for receiving a tissue sample, the outer cutting needle surrounding the inner sample needle, the outer cutting needle and the inner sample needle being arranged slidingly in relation to each other along their longitudinal direction, the outer cutting needle having a cutting end distant from the housing, and
wherein the biopsy device is adapted to, during a sampling operation whereby a tissue sample is collected in the tissue compartment of the inner sample needle, displace the outer cutting needle and the inner sample needle at least between an open position of the tissue compartment in which the tissue compartment extends beyond the cutting end of the outer cutting needle and a closed position of the tissue compartment in which the outer cutting needle covers the tissue compartment,
wherein the biopsy device includes a vacuum source for providing a pressure decrease in the tissue compartment of the inner sample needle via a vacuum channel arranged longitudinally in the biopsy needle, and
wherein the biopsy device includes a valve system adapted to provide a pressure decrease in the tissue compartment during the sampling operation, wherein the vacuum source includes a number of initially pre-evacuated vacuum containers, in that the biopsy device is adapted to, by use of a vacuum of the number of initially pre-evacuated vacuum containers, provide a pressure decrease in the tissue compartment of the inner sample needle during each one of a limited number of consecutive sampling operations, the valve system is adapted to connect each of the number of initially pre-evacuated vacuum containers separately and in succession, corresponding to the respective one of the limited number of consecutive sampling operations, with the vacuum channel in the biopsy needle; and
wherein each of the initially pre-evacuated vacuum containers is connected to a respective vacuum valve having a valve membrane, and wherein the valve system includes a hollow vacuum needle having a needle tip adapted to penetrate the valve membrane of each vacuum valve and an opposed connector end connected to the vacuum channel in the biopsy needle.

10. A biopsy device according to claim 9, wherein the respective vacuum valves are arranged along a curved path, and wherein the arrangement of the valves and the needle tip of the hollow vacuum needle are relatively displaceable so that the needle tip is positionable at each vacuum valve.

11. A biopsy device according to claim 9, wherein the vacuum source includes a cylindrical container separated into the number of initially pre-evacuated vacuum containers via internally extending partition walls, wherein the respective vacuum valves are arranged on an end wall of the cylindrical container, wherein the cylindrical container is arranged rotatably about its central axis, and wherein the needle tip of the hollow vacuum needle is arranged at a fixed position in the rotational direction of the cylindrical container.

12. A biopsy device according to claim 9, wherein the number of initially pre-evacuated vacuum containers are formed in a common housing, wherein the respective vacuum valves are arranged at the common housing along a circular arc, and wherein the needle tip of the hollow vacuum needle is arranged on a swing arm so that the needle tip is positionable at each vacuum valve.

* * * * *